(12) United States Patent
Fujishima et al.

(10) Patent No.: US 11,885,565 B2
(45) Date of Patent: Jan. 30, 2024

(54) METHOD FOR CONTROLLING FURNACE, AND ANALYZING DEVICE FOR CARRYING OUT THIS METHOD

(71) Applicant: L'Air Liquide, Société Anonyme pour l'Etude et l'Exploitation des Procédés Georges Claude, Paris (FR)

(72) Inventors: Shoichi Fujishima, Takarazuka (JP); Shigeto Uchimura, Yokosuka (JP); Kohei Nakatani, Yokosuka (JP)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 749 days.

(21) Appl. No.: 16/986,816

(22) Filed: Aug. 6, 2020

(65) Prior Publication Data

US 2021/0041173 A1 Feb. 11, 2021

(30) Foreign Application Priority Data

Aug. 6, 2019 (JP) .................................. 2019-144123

(51) Int. Cl.
*G01N 21/84* (2006.01)
*F01N 11/00* (2006.01)
(Continued)

(52) U.S. Cl.
CPC ................ *F27B 3/08* (2013.01); *C22B 7/003* (2013.01); *C22B 9/05* (2013.01); *F23J 15/027* (2013.01);
(Continued)

(58) Field of Classification Search
CPC .. G01N 33/004; G01N 33/009; G01N 1/2211; F23J 15/02; F23J 15/022;
(Continued)

(56) References Cited

U.S. PATENT DOCUMENTS 2,895,335 A * 7/1959 Kraftson .............. G01N 1/4077
73/863.12
4,912,985 A * 4/1990 Daum .................. G01N 1/2247
73/863.25
(Continued)

FOREIGN PATENT DOCUMENTS

JP 2012 500959 1/2012

*Primary Examiner* — Gregory A Wilson
(74) *Attorney, Agent, or Firm* — Elwood L. Haynes

(57) ABSTRACT

To provide a method with which it is possible to ascertain a gas concentration in a furnace rapidly, and to charge an amount of fuel and/or oxygen corresponding to the state within the furnace, and with which it is possible to reduce the device maintenance load. In order to solve the above-mentioned problem, this method for analyzing components contained in flue exhaust gas of a furnace includes: a sampling step of collecting a portion of the flue exhaust gas from a flue; a dust removal step of using a centrifugal dust collecting device to separate out dust in the flue exhaust gas collected in the sampling step, to yield an analysis gas; a measuring step of measuring components in the analysis gas to obtain the concentration of carbon monoxide in the analysis gas; and an analysis gas discharging step of causing the analysis gas to be sucked by an ejector.

3 Claims, 1 Drawing Sheet

(51) Int. Cl.
   F27B 3/08     (2006.01)
   C22B 7/00     (2006.01)
   C22B 9/05     (2006.01)
   F23J 15/02    (2006.01)
   F23N 1/02     (2006.01)
   F27D 17/00    (2006.01)
   G01N 1/40     (2006.01)
   G01N 33/00    (2006.01)
   F27D 99/00    (2010.01)

(52) U.S. Cl.
   CPC ........... F23N 1/022 (2013.01); F27D 17/004 (2013.01); G01N 1/4077 (2013.01); G01N 21/84 (2013.01); G01N 33/004 (2013.01); F23N 2900/05001 (2013.01); F23N 2900/05002 (2013.01); F23N 2900/05005 (2013.01); F27D 2099/0051 (2013.01); G01N 2001/4083 (2013.01); G01N 2201/06113 (2013.01)

(58) Field of Classification Search
   CPC ..... F23J 15/027; F27D 17/001; F27D 17/004; F27D 2017/005; F27D 17/008; F27D 2017/009; F23N 2900/05001; B01D 2258/0283; B01D 53/30; C10J 3/84
   See application file for complete search history.

(56) References Cited

U.S. PATENT DOCUMENTS

| | | | | |
|---|---|---|---|---|
| 7,223,978 | B2* | 5/2007 | Vuillermoz | G01N 21/359 |
| | | | | 250/343 |
| 7,462,218 | B2* | 12/2008 | Ducrocq | G01N 21/39 |
| | | | | 75/678 |
| 7,655,067 | B2* | 2/2010 | Lucas | C22B 9/006 |
| | | | | 75/678 |
| 9,791,360 | B2* | 10/2017 | Niemelä | G01N 15/0656 |
| 10,378,416 | B2* | 8/2019 | Higashi | G01N 1/2247 |
| 2006/0202123 | A1 | 9/2006 | Vuillermoz et al. | |
| 2011/0154949 | A1 | 6/2011 | Rheker | |

* cited by examiner

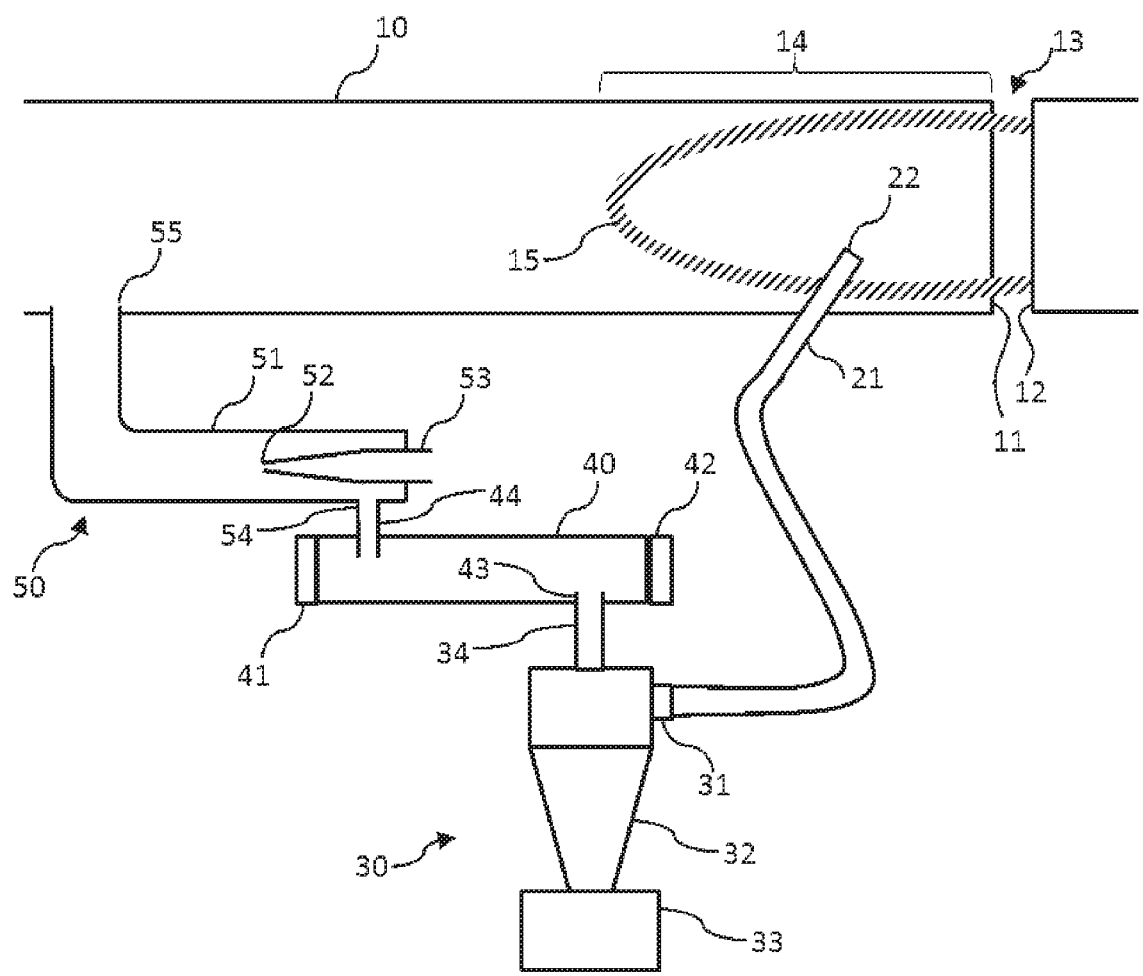

METHOD FOR CONTROLLING FURNACE, AND ANALYZING DEVICE FOR CARRYING OUT THIS METHOD

CROSS REFERENCE TO RELATED APPLICATIONS

This application claims the benefit of priority under 35 U.S.C. § 119 (a) and (b) to Japanese Patent Application No, 2019-144123, filed Aug. 6, 2019, the entire contents of which are incorporated herein by reference.

BACKGROUND

Technical Field

The present invention relates to a method for measuring gas generated in a furnace, in particular an incinerator or a furnace for melting metal, in order to control the furnace, a control method based on measurement results obtained by means of said measuring method, and a measuring device.

Background Art

Metal, refuse, and the like are melted or incinerated in a furnace into which fuel and an oxidizing agent are introduced.

There is a known method for adding an additive containing carbon, such as coal, in a step in which fuel and oxygen are introduced into a melting furnace to melt metal. When an additive is added, the amount of carbon monoxide generated in the furnace increases, and the temperature of the exhaust gas rises accordingly. This is because when carbon monoxide is discharged as exhaust gas, the carbon monoxide mixes with the atmospheric air or the like and burns. However, carbon monoxide can be used as fuel in the furnace.

Accordingly, a method has been proposed in which the amount of fuel and oxidizing agent to be introduced into the furnace are optimized by measuring the exhaust gas temperature to detect an increase in the amount of carbon monoxide generated in the furnace (Patent Literature 1).

Further, an analysis method employing a laser optical analyzer has also been proposed as a method for measuring the amount of carbon monoxide and/or carbon dioxide in the exhaust gas (Patent Literature 2).

Now, when metal, refuse, or the like, are being charged into a furnace, flammable gas such as carbon monoxide may suddenly be generated, even in a step in which organic matter such as coal is not added. This is because if the amount of plastic or the like that is charged increases, or if material to be melted or incinerated is charged while organic matter is attached thereto, the organic matter volatilizes when the temperature inside the furnace reaches a high temperature. However, unlike in a step in which the timing and amount of coal to be charged is known in advance, since the amount of organic matter attached to the metal or the like varies, the time at which the carbon monoxide is generated, and the amount thereof also vary.

It is therefore desirable to monitor the content of carbon monoxide and carbon dioxide, for example, in the exhaust gas, and to reflect the measurement results in the control of the amounts of fuel and oxygen to be charged.

Accordingly, as disclosed in patent literature article 2, it is conceivable to collect a portion of the exhaust gas flowing through a furnace flue, and to measure the amounts of carbon monoxide, carbon dioxide and the like using a laser optical analyzer. In this method, analysis gas collected through a narrow tube from the exhaust gas flow passage is introduced into a gas cell of the laser optical analyzer. Since the analysis gas contains a large amount of dust, the dust is removed using a filter before being introduced into the gas cell.

In this method, since it takes time to reach the gas cell, there is a problem in that a time lag occurs between the generation of the carbon monoxide and the detection thereof. There is also a problem in that it is necessary to shut down the entire device or to switch to a bypass line in order to carry out maintenance of pumps and filters, and this results in downtime and a considerable amount of maintenance work.

In order to shorten the time lag, it is conceivable to increase the degree of vacuum using a pump disposed downstream of the gas cell, to increase the flow velocity of the analysis gas.

However, when the pressure of the analysis gas is low, if there is a leak point in the analysis gas flow passage there is a problem in that the amount of outside air taken in increases, and the measurement results become inaccurate. Further, if the flow velocity of the analysis gas increases, the analysis gas passes through the analysis gas flow passage with the high temperature thereof maintained, leading to thermal contraction of the analysis gas flow passage, and leaks are more liable to occur.

If the flow velocity of the analysis gas is increased, the amount of dust and the like that is sucked in increases, causing frequent filter clogging due to dust. There is thus a problem in that the frequency of filter replacement, pipe cleaning, and maintenance such as purging with gas increases.

If the flow velocity of the analysis gas is increased, the analysis gas reaches the filter while remaining at a high temperature, and there is thus also the problem that the filter is damaged.

However, decreasing the temperature of the analysis gas causes condensation of moisture in the analysis gas, and is thus not preferable. This is because condensed water attaches to the filter, and dust attaches to the condensed water, further increasing the frequency at which the filter becomes clogged. It is also conceivable to heat the pipes or to provide a moisture removing step in order to suppress the generation of condensed water, but this increases the complexity of the device and the process.

In the light of the abovementioned background, with a conventional method, even if the temperature and the gas concentration are measured, variations over time in the measurement results occur as a result of a delay in the timing at which the amount of introduced fuel is reduced (or the timing at which the amount of introduced oxygen is increased), and filter blocking, for example. It has therefore not been possible for the energy efficiency to be improved sufficiently by adjusting the concentrations of fuel and oxygen in the furnace to optimal values.

Accordingly, there has been a desire to develop a method with which it is possible to ascertain the gas concentration in the furnace rapidly, and to charge an amount of fuel and/or oxygen corresponding to the state within the furnace, and with which it is possible to reduce the device maintenance load.

Patent Documents

Patent Literature 1 WO 2012/500959
Patent Literature 2 US 2006/0202123

SUMMARY

An analysis method according to the present invention, for overcoming the above-mentioned problem, is
a method for analyzing components contained in flue exhaust gas of a furnace, including:
a sampling step of collecting a portion of the flue exhaust gas from a flue;
a dust removal step of using a centrifugal dust collecting device to separate out dust in the flue exhaust gas collected in the sampling step, to yield an analysis gas;
a measuring step of measuring components of the analysis gas to obtain the concentration of carbon monoxide in the analysis gas; and
an analysis gas discharging step of causing the analysis gas to be sucked by an ejector.

In the analysis method, the flow rate of the flue exhaust gas collected in the sampling step may be at least equal to 100 L/min, and the flow velocity thereof may be at least equal to 0.1 m/s.

A furnace control method according to the present invention is a method for adjusting the flow rate of fuel and/or an oxidizing agent introduced into the furnace on the basis of an analysis result obtained using the abovementioned analysis method.

In the control method, control may be carried out to reduce the flow rate of the fuel introduced into the furnace if the carbon monoxide concentration obtained in the measuring step increases.

In the control method, control can also be carried out to increase the flow rate of the oxidizing agent introduced into the furnace if the carbon monoxide concentration obtained in the measuring step increases.

An analysis system according to the present invention is an analysis system for analyzing components contained in flue exhaust gas of a furnace, including:
a probe having a gas intake port for collecting a portion of the flue exhaust gas flowing through the flue; a centrifugal dust collector which separates out dust in sample gas collected in the probe, to yield an analysis gas;
a measuring device for measuring components in the analysis gas to obtain the concentration of carbon monoxide in the analysis gas; and
an ejector for sucking the analysis gas from the measuring device.

The probe in the analysis system may be disposed in a central part of the flue, in an upstream portion of the flue, on an upstream side of a position (referred to as 'combustion position' hereinbelow) at which gas generated inside the furnace and air around the analyzing device mix. The probe may be a water-cooled probe.

The diameter of an opening portion of the gas intake port in the analysis system can be at least equal to 3 mm and at most equal to 100 mm.

The centrifugal dust collector in the analysis system may have a gas introduction chamber in which a plurality of separation containers are disposed in parallel.

The measuring device in the analysis system may be a wavelength tunable semiconductor laser device which measures the content of at least one chemical species among carbon monoxide and carbon dioxide.

The ejector in the analysis system may be
an ejector which utilizes the flow of a driving fluid to suck the analysis gas,
the driving fluid is an inert gas, and
the flow rate of the driving fluid ejected from an ejection port provided inside the ejector may be at least equal to 0.01 times and at most equal to 1 times the flow rate of the analysis gas.

A furnace according to the present invention is
a furnace including the abovementioned analysis system, wherein
the flow rate of fuel and/or an oxidizing agent introduced into the furnace is controlled on the basis of the carbon monoxide concentration obtained by the analyzing device.

The furnace may be an electric furnace for melting a material including at least one species among the following metal elements:
a) iron,
b) aluminum,
c) manganese,
d) tin,
e) zinc,
f) lead, and
g) copper.

According to the analysis method employing the abovementioned analyzing device, since dust can be separated from the analysis gas by means of the centrifugal dust collecting device, it is not necessary to install a dust removal filter in an analysis gas line.

Further, since a large amount of gas can be sucked with a low vacuum by means of the ejector, it is possible to reduce the time lag until the collected flue exhaust gas is analyzed as the analysis gas in the measuring step. Here, a low vacuum refers to a pressure at least equal to −3 kPa and less than atmospheric pressure.

According to the analysis method of the present invention, there is little pressure difference between the inside and the outside of the gas flow passage, and the amount of the analysis gas introduced into the gas cell is large, and therefore even if a leak occurs in the gas flow passage, the impact on the analysis values can be reduced. The generation of carbon-containing gas in the furnace can therefore be detected in a short time period after the gas is generated, and the concentration thereof can be measured with high precision.

With a furnace provided with the analyzing device described hereinabove, an optimal amount of fuel and/or oxidizing agent can be charged into the furnace at a suitable timing, on the basis of the measurement results, and therefore energy efficiency can be improved.

BRIEF DESCRIPTION OF THE DRAWING

For a further understanding of the nature and objects for the present invention, reference should be made to the following detailed description, taken in conjunction with the accompanying drawings, in which like elements are given the same or analogous reference numbers and wherein:

FIG. 1 is a drawing illustrating a configuration example of an analysis system according to the present invention.

DETAILED DESCRIPTION OF THE PREFERRED EMBODIMENTS

The analysis method according to the present invention is a method for analyzing components contained in flue exhaust gas of a furnace, in particular an incinerator or a melting furnace for melting metal.

In an incinerator, fuel and an oxidizing agent are introduced, and combustible refuse such as paper and plastics is incinerated. Here, if the amount of organic matter and the like that is charged increases, the amount of carbon-containing components in the gas in the furnace increases. This is because the carbon-containing components are volatilized when the organic matter and the like reaches a high temperature in the furnace. Carbon-containing components, namely carbon monoxide, hydrocarbons, and mixtures thereof, can be utilized as fuel, and the amount of fuel charged into the furnace can be reduced correspondingly.

In a melting furnace, fuel and an oxidizing agent are introduced, and metal is melted. Here, if organic matter such as oil, a label, or paint is attached to the metal, the organic matter volatilizes upon reaching a high temperature in the furnace, and the amount of carbon-containing components in the gas in the furnace increases. The amount of fuel charged into the furnace can also be reduced in this case, in the same way as in an incinerator.

In both incinerators and melting furnaces, if the amount of carbon-containing components that can be utilized as fuel increases, it is also possible to maintain the amount of fuel charged into the furnace, and to increase the amount of the oxidizing agent charged into the furnace.

The amount of fuel and/or oxidizing agent charged into the furnace in this way is preferably controlled in accordance with a variation in the concentration of the carbon-containing components in the furnace.

Accordingly, the analysis method of the present invention includes: a sampling step of collecting a portion of the flue exhaust gas from a flue; a dust removal step of using a centrifugal dust collecting device to separate out dust in sample gas collected in the sampling step, to yield an analysis gas; a measuring step of measuring components of the analysis gas to obtain the concentration of carbon monoxide in the analysis gas; and an analysis gas discharging step of causing the analysis gas to be sucked by an ejector. The details are described below.

Sampling Step

In the sampling step, a portion of the exhaust gas flowing through the flue of the furnace is collected from the probe.

As illustrated in FIG. 1, an inlet portion 11 positioned upstream of the flue 10 is provided in close proximity to an exhaust gas outlet 12 of the furnace (which is not shown in the drawing), but there is a gap 13 between the inlet portion and the exhaust gas outlet 12. Atmospheric air flows in from the gap 13 towards the inside of the flue 10, and mixes with the exhaust gas and is burned, thereby forming a flame (the part represented by the oblique lines in FIG. 1) in an upstream portion 14 of the flue 10. The position of the flame is referred to as a combustion position 15. A gas intake port 22 of a probe 21 for collecting a portion of the flue exhaust gas is disposed in a central part of the flue 10 on the upstream side of the combustion position 15.

The main components contained in the flue exhaust gas are carbon monoxide and carbon dioxide. At the combustion position 15, flammable carbon-containing components (such as carbon monoxide) contained in the flue exhaust gas mix with oxygen in the atmospheric air and burn. The concentration of carbon monoxide on the downstream side of the combustion position 15 is therefore lower than inside the furnace. Therefore, in order for the concentration of the carbon monoxide inside the furnace to be measured accurately, the flue exhaust gas must be collected upstream of the combustion position 15.

Since the temperature of the flue exhaust gas is high, approximately 1000° C. to 1600° C., a configuration for cooling by means of a fluid may be adopted to protect the probe 21 (which is typically made from metal). For example, a water cooled probe that is cooled using water can be employed.

The flow velocity and the flow rate when the flue exhaust gas is collected are determined by the diameter of the opening portion of the gas intake port 22 and the suction capability of the ejector 50, but the flow velocity may be at least equal to 0.1 m/s and at most equal to 20 m/s, and is preferably at least equal to 2 m/s and at most equal to 13 m/s. The flow rate may be at least equal to 100 L/min and at most equal to 2000 L/min, and is preferably at least equal to 650 L/min and at most equal to 1000 L/min.

The higher the flow velocity, the better the analysis response, which is preferable. For example, the flow velocity is preferably adjusted such that the time from when the flue exhaust gas is sucked into the probe 21 until the flue exhaust gas is discharged from an analysis cell 40 for carrying out measurement is short, approximately 3 to 5 seconds.

However, if the diameter of the opening portion of the gas intake port 22 is reduced in order to increase the flow velocity, blocking of the gas intake port 22 and the probe 21 due to the effects of dust and the like becomes a problem. Further, if the suction capability of the ejector 50 is increased in order to increase the flow velocity, the amount of the driving fluid of the ejector 50 that is consumed increases, which is not economical.

Accordingly, upon investigating the optimal ranges for the diameter of the opening portion of the gas intake port 22 and the suction capability of the ejector 50, it was found that the diameter of the opening portion may be at least equal to 3 mm and at most equal to 100 mm, preferably at least equal to 10 mm and at most equal to 75 mm, and more preferably at least equal to 20 mm and at most equal to 50 mm.

Further, the flow rate of the driving fluid of the ejector 50 can be at least 0.01 times and at most 1 times the flow rate of the analysis gas discussed hereinafter.

As described hereinabove, the flue exhaust gas collected by the probe 21 is fed to the centrifugal dust collecting device 30.

It should be noted that it is also conceivable to heat the gas cell 40 to suppress the generation of condensation in the probe 21 and in the pipe from the probe 21 to the centrifugal dust collecting device 30. This is because, if condensation occurs, dust is liable to become attached to the condensed water, blocking the pipe. However, since the flow velocity of the analysis gas in the present invention is sufficiently high for the temperature of the flue exhaust gas to remain at a high temperature until reaching the centrifugal dust collecting device 30, it is not necessary to perform heating. It is therefore not necessary to provide a heating mechanism for the probe 21 and the pipe from the probe 21 to the centrifugal dust collecting device 30.

Dust Removal Step

The dust removal step is a step of removing dust in the flue exhaust gas collected in the sampling step, by separating out the dust using the centrifugal dust collecting device 30.

The flue exhaust gas containing dust, such as soot generated in the furnace, is introduced from the probe 21 into a separation container 32 of the centrifugal dust collecting device 30 through a gas inflow port 31. The separation container 32 is a cylindrical or conical container that stands vertically. The flue exhaust gas flows into the separation container 32 in a tangential direction to generate a swirling velocity component. Since the density of the dust is greater than that of the gas component, the dust is carried towards the wall surface of the separation container 32 by means of a centrifugal force generated by the swirling, and then collects in a dust container 33. Meanwhile, the gas from which the dust has been removed is fed to the gas cell 40 from a central inner pipe 34, as the analysis gas.

The dust that has been collected in the dust container 33 is disposed of as necessary. A valve may be provided between the separation container 32 and the dust container 33, and the dust may be extracted from the dust container 33 after the valve has been closed.

It should be noted that the centrifugal dust collecting device may be of the single cylinder type having one separation container, but it may also be configured to include a gas introduction chamber in which a plurality of separation containers are arranged in parallel. With a system in which a plurality of separation containers are arranged, the dust collecting effect can be improved compared with a system having a single separation container. A configuration including a plurality of separation containers may therefore be employed if there is a large amount of dust.

Measuring Step

The measuring step is a step of measuring the components of the analysis gas introduced into the gas cell 40, and measuring the concentration of carbon monoxide in the analysis gas. There is no particular restriction to the components in the furnace of which the concentration is to be measured, and may be components of one or more species selected from the group comprising carbon monoxide, carbon dioxide, methane, and oxygen. The carbon monoxide concentration may be measured directly, but can also be measured indirectly. For example, since the main components of the flue exhaust gas are carbon dioxide and carbon monoxide, the concentration of carbon monoxide can be obtained by measuring the concentration of carbon dioxide and subtracting the result from the whole. The carbon monoxide concentration may be calculated after a measurement has been made including gases contained in the flue exhaust gas other than carbon monoxide and carbon dioxide (for example moisture, and hydrocarbon components such as methane, derived from the fuel).

There is no particular restriction to the measuring method provided that it is a method with which the abovementioned components can be measured, and for example a wavelength tunable semiconductor laser device may be used.

length can, for example, be at least equal to 0.7 m and at most equal to 5 m, and preferably at least equal to 1 m and at most equal to 2.5 m. The thickness can, for example, be a diameter at least equal to 10 mm and at most equal to 100 mm, and preferably at least equal to 10 mm and at most equal to 80 mm.

It is also possible to heat the gas cell 40 in order to suppress the generation of condensation in the gas cell 40. However, since the flow velocity of the analysis gas in the present invention is sufficiently high for the temperature of the analysis gas to remain at a high temperature until passing through the gas cell 40, it is not necessary to perform heating. If the temperature of the analysis gas discharged from the gas cell 40 is at least equal to 80° C., it is not necessary to perform heating.

Analysis Gas Discharging Step

The analysis gas discharging step is a step of causing the analysis gas to be sucked by the ejector 50. In the method for introducing the analysis gas into the gas cell 40 of the analyzing device, the analysis gas in the gas cell 40 is sucked. The ejector 50 is provided with a case 51 inside which a space is formed, a nozzle 53 for ejecting the driving fluid from an ejection port 52 into the case 51, and a suction port 54 connected to the outlet 44 of the gas cell 40. The analysis gas, which is a driven fluid, is introduced from the suction port 54 into the case 51, and is sucked by the driving fluid ejected from the ejection port 52.

The driving fluid and the analysis gas are discharged from the discharge port 55 of the ejector 50 and merge in a latter stage of the flue 10.

An inert gas used as the driving fluid should be a gas that is inert with respect to the analysis gas, and may, for example, be a gas having an oxygen concentration at most equal to 3%, or may, for example, be nitrogen gas, argon gas, carbon dioxide gas or a mixed gas thereof.

The flow rate of the driving fluid can be determined in accordance with the flow rate of the analysis gas and the opening surface area of the ejection port 52, for example, and can, for example, be at least 0.01 times and at most 1 times, and preferably at least 0.05 times and at most 0.5 times the flow rate of the analysis gas.

Table 1 presents specific examples in which the time taken for gas generated in the furnace to reach the gas cell 40 of the measuring device is calculated for cases in which the analysis method described hereinabove is used.

TABLE 1

| Opening portion diameter of probe gas intake port (mm) | Flow rate of flue exhaust gas collected by probe (m³/hr) | Flow velocity of flue exhaust gas collected by probe (m/sec) | Flow rate of ejector driving fluid (m³/hr) | Degree of vacuum in gas cell 40 (kPa) | Length to reach gas cell 40 (m) | Time to reach gas cell 40 (sec) |
|---|---|---|---|---|---|---|
| 25 | 50 | 30 | 9 | −3 | 8 | 1.26 |
| 25 | 64 | 39 | 12 | −2.9 | 8 | 1.1 |
| 25 | 72 | 44 | 15 | −2.8 | 8 | 0.98 |

In FIG. 1, a laser light source is disposed in one end portion (41 or 42) of the cylindrical gas cell 40 and a receiving unit is disposed in the other end portion (42 or 41). The analysis gas introduced from an inlet 43 of the gas cell 40 is sucked from an outlet 44 into the ejector 50.

The length and thickness of the gas cell 40 can be defined arbitrarily in accordance with the analyzing device being used and the required measurement sensitivity, and the With a conventional method not employing the analysis system according to the present invention, in which exhaust gas is sucked from a probe inserted into the flue, the components of the gas after removal of dust using a filter are analyzed, and the gas after analysis is discharged using a vacuum pump, the flow rate of the exhaust gas passing through the probe is approximately 10 L/min, and the diameter of the opening portion of the gas intake port of the probe is approximately 25 mm. Pump performance and the like make it difficult to increase the flow rate and the flow velocity. With such a conventional analysis method, the measurement time lag is large.

Further, whereas in a conventional method a vacuum pump is used to bring the pressure in the gas cell to a high vacuum of approximately −70 kPa, when the analysis system according to the present invention is employed, it is possible to set the pressure in the gas cell 40 to a low vacuum of less than −3 kPa without using a vacuum pump.

Furnace Control Method

A furnace control method for adjusting the flow rate of the fuel and/or the oxidizing agent on the basis of the analysis results obtained by the analysis method described hereinabove will now be described.

The fuel and the oxidizing agent are charged into the furnace in accordance with a charging state of the material to be incinerated or melted. The fuel is an organic compound such as a hydrocarbon, and may be a liquid fuel such as oil, or a gaseous fuel such as natural gas. The oxidizing agent may be oxygen gas, or may be a mixed gas containing at least 20% oxygen gas.

If the carbon monoxide concentration obtained in the measuring step increases, it is possible to (1) reduce the flow rate of the fuel introduced into the furnace, (2) increase the flow rate of the oxidizing agent introduced into the furnace, or implement both (1) and (2).

An increase in the concentration of the carbon monoxide in the analysis gas indicates an increases in the amount of carbon monoxide generated in the furnace. Since carbon monoxide acts as a fuel in the furnace, reducing the introduced amount of fuel by a corresponding amount makes it possible to operate the furnace using an optimal amount of introduced fuel.

If the flow rate of the introduced fuel is kept constant, increasing the amount of oxidizing agent that is introduced, to accompany the increase in the concentration of carbon monoxide, enables the carbon monoxide to be used effectively as fuel, without being discharged to the outside of the furnace in an unburned state.

In a steady state, the amount of fuel introduced into the furnace is determined in advance. If the concentration of carbon monoxide increases, control is performed to reduce the amount of fuel introduced into the furnace in accordance with a calorific value corresponding to the amount of said increase.

The calorific value corresponding to the amount of increase in carbon monoxide can be obtained by multiplying the concentration of the carbon monoxide by the spatial volume of the furnace and the calorific value per unit volume of carbon monoxide. Here, the spatial volume of the furnace refers to a volume obtained by subtracting the volume of the material to be incinerated/melted in the furnace from the volume of the furnace.

Performing control such that said calorific value is equivalent to the calorific value corresponding to the amount of decrease in fuel introduced into the furnace enables the carbon monoxide generated in the furnace to be used effectively. Since the calorific value per unit volume of the fuel introduced into the furnace is known, the amount of decrease in the fuel to be introduced into the furnace can be varied in accordance with the following formula (1), on the condition that the carbon monoxide lies within a combustible range. Here, the combustible range of carbon monoxide is a carbon monoxide concentration of at least 12.5% and at most 74% in air, and at least 15.5% and at most 94% in pure oxygen. In the case of a mixed atmosphere of air and pure oxygen, the values of the combustible range of carbon monoxide lie between these two ranges, and if, for example, the oxygen concentration is 40%, the combustible range is at least 13% and at most 80%. It should be noted that if the amount of carbon monoxide lies outside the combustible range, control is performed such that the amount of introduced fuel does not vary.

$$\text{(Amount of decrease in fuel)} = \text{(concentration of carbon monoxide)} \times \text{(spatial volume of furnace)} \times \text{(calorific value per unit volume of carbon monoxide)} \times \text{(first coefficient)} \div \text{(replacement time for amount of exhaust gas with respect to spatial volume in furnace)} \div \text{(calorific value per unit volume of fuel)} \quad (1)$$

Here the first coefficient is a value that varies in accordance with the carbon monoxide combustion efficiency. If the carbon monoxide concentration is at least equal to 12.5% and at most equal to 74% (in air), or is at least equal to 15.5% and at most equal to 94% (in pure oxygen), then when the carbon monoxide concentration is low, the first coefficient can be close to 0.03, and when the carbon monoxide concentration is high, the first coefficient can have a value of less than 0.03. For example, in the case of combustion in air, if the carbon monoxide concentration is at least equal to 0% and less than 12.5% or is greater than 74%, the first coefficient can be set to 0, and if the carbon monoxide concentration is at least equal to 12.5% and at most equal to 74%, the first coefficient can be set to be at least equal to 0 and at most equal to 0.03. Further, in the case of combustion in pure oxygen, if the carbon monoxide concentration is at least equal to 0% and less than 15.5% or is greater than 94%, the first coefficient can be set to 0, and if the carbon monoxide concentration is at least equal to 15.5% and at most equal to 94%, the first coefficient can be set to be at least equal to 0 and at most equal to 0.03. Further, if the concentration of both carbon dioxide and carbon monoxide is being measured, the concentration ratio between carbon dioxide and carbon monoxide may be reflected in the first coefficient.

Further, here the replacement time of the amount of exhaust gas with respect to the spatial volume in the furnace refers to a time obtained by dividing the spatial volume in the furnace by an amount obtained by subtracting an outside air inflow rate from the exhaust gas suction capability of the dust collector or the like.

Table 2 presents an example in which the amount of decrease in fuel (natural gas 13A is used in the example in Table 2) is obtained from the carbon monoxide concentration in accordance with formula (1).

TABLE 2

| | Carbon monoxide concentration | Spatial volume in furnace | Calorific value per unit volume of carbon monoxide | First coefficient | Replacement (retention) time for space in furnace due to exhaust gas suction | Calorific value per unit volume of fuel | Amount of decrease in fuel |
|---|---|---|---|---|---|---|---|
| Unit | % | m³ | kcal/m³ | — | sec. | kcal/m³ | m³/hr |
| | a | b | c | d | e | f | a/100*b*c*d/e*3600/f |
| Less than lower limit of combustible range | 10 (In air) | 100 | 3.020 | 0 | 3 | 9.950 | 0 |
| Incombustible range | 30 (In air) | 100 | 3.020 | 0.025 | 3 | 9.950 | 273 |
| Incombustible range | 60 (In air) | 100 | 3.020 | 0.023 | 3 | 9.950 | 503 |
| Above upper limit of combustible range | 80 (In air) | 100 | 3.020 | 0 | 3 | 9.950 | 0 |

Similarly, the amount of increase in the oxidizing agent to be introduced into the furnace may be varied in accordance with the following formula (2). It should be noted that if the amount of carbon monoxide is less than the lower limit of the combustible range, control is performed such that the amount of introduced oxygen does not vary.

(Amount of increase in oxidizing agent)=(carbon monoxide concentration)×(spatial volume of furnace)÷(replacement time of exhaust gas amount with respect to spatial volume in furnace)×(stoichiometric ratio of oxidizing agent to carbon monoxide)    (2)

Here, a second ratio is a value that varies in accordance with the carbon monoxide combustion efficiency. If the carbon monoxide concentration is at least equal to 12.5% (in air), or is at least equal to 15.5% (in pure oxygen), then when the carbon monoxide concentration is low, the second coefficient can be close to 0.03, and when the carbon monoxide concentration has a high value, the second coefficient can have a value of less than 0.03. Meanwhile, if the carbon monoxide concentration is less than the lower limit of the combustible range, namely less than 12.5% (in air) or less than 15.5% (in pure oxygen), the second coefficient is 0. Conversely, if the carbon monoxide concentration exceeds the upper limit of the combustible range, namely more than 74% (in air), or more than 94% (in pure oxygen), then control may be performed to increase the second coefficient temporarily to approximately 0.03 and to increase the amount of oxidizing agent such that the carbon monoxide lies in a concentration range in which combustion is possible.

Further, the stoichiometric ratio of the oxidizing agent to carbon monoxide is a value obtained by dividing the coefficient of the oxidizing agent in a carbon monoxide combustion reaction formula by the coefficient of the carbon monoxide.

Table 3 presents an example in which the amount of increase in the oxidizing agent is obtained from the carbon monoxide concentration in accordance with formula (2). It should be noted that oxygen gas is used as the oxidizing agent in the example in Table 3. Since carbon monoxide and oxygen burn in accordance with the formula $2CO+O_2 \rightarrow 2CO_2$, the stoichiometric ratio of the oxidizing agent (oxygen) to carbon monoxide when oxygen is used is ½.

TABLE 3

| | Carbon monoxide concentration | Spatial volume in furnace | Second coefficient | Replacement (retention) time for space in furnace due to exhaust gas suction | Stoichiometric ratio of oxidizing agent to carbon monoxide | Amount of increase in oxidizing agent |
|---|---|---|---|---|---|---|
| Unit | % | m³ | — | sec. | kcal/m³ | m³/hr |
| | a | b | c | d | e | a/100*b*c/d*3600*e |
| Less than lower limit of combustible range | 10 (In air) | 100 | 0 | 3 | 1/2 | 0 |
| Incombustible range | 30 (In air) | 100 | 0.028 | 3 | 1/2 | 504 |
| Incombustible range | 60 (In air) | 100 | 0.026 | 3 | 1/2 | 936 |
| Above upper limit of combustible range | 80 (In air) | 100 | 0.03 | 3 | 1/2 | 1440 |

Applicable conditions for adjusting the flow rate of the fuel or oxygen are that the temperature of the space in the furnace is at least equal to 605° C. and preferably at least equal to 850° C., and that the replacement (retention) time for the space in the furnace due to exhaust gas suction is at least equal to 1 second and preferably at least equal to 2 seconds.

EXPLANATION OF THE REFERENCE CODES

10 Flue
11 Inlet portion
12 Exhaust gas outlet
13 Gap
14 Upstream portion (of flue)
15 Combustion position
21 Probe
22 Gas intake port
30 Centrifugal dust collecting device
31 Gas inflow port
32 Separation container
33 Dust container
34 Inner pipe
40 Analysis cell
43 Inlet (of gas cell)
44 Outlet (of gas cell)
50 Ejector
51 Case (of ejector)
52 Ejection port
53 Nozzle
54 Discharge port (of ejector)

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. An analysis system for analyzing components contained in flue exhaust gas of a furnace, comprising a probe having a gas intake port for collecting a portion of the flue exhaust gas flowing through the flue;
   a centrifugal dust collector which separates out dust in sample gas collected in the probe, to yield an analysis gas;
   a measuring device for measuring components in the analysis gas to obtain the concentration of carbon monoxide in the analysis gas; and
   an ejector for evacuating the analysis gas from the measuring device,
   wherein the ejector is
      an ejector which utilizes the flow of a driving fluid to evacuate the analysis gas,
      the driving fluid is an inert gas, and
      the flow rate of the driving fluid ejected from an ejection port provided inside the ejector may be at least equal to 0.01 times and at most equal to 1 times the flow rate of the analysis gas.

2. An analysis system for analyzing components contained in flue exhaust gas of a furnace, comprising a probe having a gas intake port for collecting a portion of the flue exhaust gas flowing through the flue;
   a centrifugal dust collector which separates out dust in sample gas collected in the probe, to yield an analysis gas;
   a measuring device for measuring components in the analysis gas to obtain the concentration of carbon monoxide in the analysis gas; and
   an ejector for evacuating the analysis gas from the measuring device,
   wherein the flow rate of fuel and/or an oxidizing agent introduced into the furnace is controlled on the basis of the carbon monoxide concentration obtained by the analyzing device.

3. The furnace according to claim 2, wherein the furnace is an electric furnace for melting a material including at least one species among the following metal elements:
   a) iron,
   b) aluminium,
   c) manganese,
   d) tin,
   e) zinc,
   f) lead, and
   g) copper.

* * * * *